US00PP24504P3

(12) United States Plant Patent
Korlipara

(10) Patent No.: US PP24,504 P3
(45) Date of Patent: May 27, 2014

(54) ***ECHINACEA* PLANT NAMED 'SECRET LOVE'**

(50) Latin Name: ***Echinacea* spp.**
Varietal Denomination: Secret Love

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 100 days.

(21) Appl. No.: 13/573,349

(22) Filed: Sep. 11, 2012

(65) Prior Publication Data

US 2014/0075636 P1 Mar. 13, 2014

(51) Int. Cl.
*A01H 5/00* (2006.01)

(52) U.S. Cl.
USPC ..... Plt./428; Plt./263.1

(58) Field of Classification Search
USPC ..... Plt./263.1, 428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'Secret Love' characterized by enlarged disc florets forming an anemone-type inflorescence, red disc and ray florets, a medium sized, mounding habit with good stem count and branching, and excellent vigor.

1 Drawing Sheet

Botanical denomination: *Echinacea* spp.
Variety designation: 'Secret Love'.

BACKGROUND OF THE INVENTION

The present invention relates to a new and distinct cultivar of *Echinacea* and given the cultivar name 'Secret Love'. *Echinacea* is in the family Asteraceae. This new cultivar is a fifth generation seeding originating from a planned breeding program using *Echinacea paradoxa* (an unpatented plant) as the seed parent in the original cross and *Echinacea purpurea* 'Ruby Giant' (an unpatented plant) as the pollen parent. The exact parents of this selection are unknown, unnamed, proprietary plants.

Compared to *Echinacea* 'Hot Papaya' (U.S. Plant Pat. No. 21,022), the new cultivar has inflorescences that are red rather than orangey red. The new cultivar has a shorter habit and the inflorescences are smaller with shorter and tighter disc florets.

Compared to the photo of *Echinacea* 'Eccentric' (U.S. Plant Pat. No. 23,979) viewed online, the new cultivar has shorter ray florets.

Compared to *Echinacea* 'Cinnamon Cupcake' (U.S. Plant patent application Ser. No. 13/573,341), the new cultivar is taller.

This new *Echinacea* cultivar is distinguished by:

1. enlarged disc florets forming an anemone-type inflorescence,
2. red disc and ray florets,
3. a medium sized, mounding habit with good stem count and branching, and
4. excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a group of one-year-old *Echinacea* 'Secret Love' plants growing in the garden in full sun in early August in Canby, Oreg.

DETAILED PLANT DESCRIPTION

The following is a detailed description of the new *Echinacea* cultivar based on observations of 10-month-old specimens growing in the trial bed in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart*, $5^{th}$ edition.

Plant:

*Type*.—Herbaceous perennial.
*Hardiness*.—USDA Zones 4 to 9.
*Size*.—Grows to about 50 cm wide and 60 cm tall to top of inflorescences.
*Form*.—Basal clump, with about 9 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 6 inflorescences per stem.
*Size*.—To 58 cm tall to a terminal inflorescence and 6 mm wide at base.
*Internode length*.—5 cm to 11 cm.
*Surface texture*.—Strigose.
*Color*.—Yellow Green 146C speckled with Greyed Purple 187A.

Leaf (basal):

*Type*.—Simple.

*Shape*.—Lanceolate.

*Arrangement*.—Basal.

*Blade size*.—Grows to 16 cm long and 6.5 cm wide.

*Margins*.—Coarsely serrate.

*Apex*.—Acuminate.

*Base*.—Attenuate.

*Surface texture*.—Strigose on both sides.

*Venation*.—Pinnate, with 3 main veins.

*Color*.—Topside Green N137A bottom side closest to Yellow Green 147B.

*Petiole description*.—Grows to 20 cm long and 5 mm wide, strigose, Yellow Green 146B tinted Greyed Purple 187A.

Leaf (stem):

*Type*.—Simple.

*Shape*.—Lanceolate.

*Arrangement*.—Alternate.

*Blade size*.—Grows to 14 cm long and 5.8 cm wide.

*Margins*.—Coarsely serrate.

*Apex*.—Acuminate.

*Base*.—Attenuate.

*Surface texture*.—Strigose on both sides.

*Venation*.—Pinnate, with 3 main veins from the base.

*Color*.—Topside Yellow Green N137A with main vein Yellow Green 145D, bottom side closest to Yellow Green 147B.

*Petiole description*.—On all but upper leaves, clasping, grows to 11 cm long and 6 mm wide above the clasp, sparsely strigose, Yellow Green 146D with base tinted Greyed Purple 187A.

Inflorescence:

*Type*.—Composite on terminal stalked heads.

*Number of flowering stems from the ground*.—About 9.

*Flowering stem*.—Grows to 58 cm tall from the base of the plant to the terminal inflorescence and can grow to 8 cm long from the top stem leaf to the base of an inflorescence; branched with 1 to 6 inflorescences per stem; diameter growing to 8 mm wide near the inflorescence; strigose; Yellow Green 146C blotched and tinted with Greyed Purple 187A.

*Size*.—Grows to 7 cm wide and 6 cm deep as disc enlarges.

*Form*.—Ray florets held reflexed, mature disc is conic.

*Immature inflorescence*.—Grows to 3.5 cm wide and 1.5 cm deep, ray florets held at a 40 degree angle from the vertical and rolled up so only the back color shows, florets Greyed Purple 187C with tips Yellow Green 145A, center Yellow Green 145A.

*Ray florets*.—About 20 in number, grow to 36 mm long and 8 mm wide, oblanceolate with the tip two to three-toothed (each acute), entire margins, base attenuate, glabrous on both sides; topside Red 46A, bottom side Greyed Red 181A; each with 1 pistil and 4 reduced stamen, ovary 3 mm long, White 155A, style 7 mm long Greyed Purple 187D, 2-branched stigma spreading, Greyed Purple 187A; reduced stamen 2 mm long, threadlike, Yellow Green 145D, anthers reduced, pollen none.

*Disc*.—Flat becoming conic, growing to 33 mm deep and 70 mm wide with maturity, Red 46A.

*Linear bracts next to each ray and disc florets*.—1 per floret, stiff, linear, persistent, 11 mm long with the top 1 mm Greyed Purple 187A, the next 2 mm Greyed Purple 187C, Yellow Green 144A in middle, then Yellow Green 145D on bottom ⅓.

*Disc florets*.—About 280 in number, grow to 28 mm long and 8 mm wide, corollas 23 mm long and 8 mm wide, tubular at base then flattens to 1 lanceolate petal with 3 terminal teeth, glabrous, margins entire, tips acuminate, topside Red 46A, bottom side Greyed Red 181A; each floret with 1 pistil and 4 reduced stamen, ovary 3 mm long, White 155A, style 7 mm long Greyed Purple 187D, 2-branched stigma spreading, Greyed Purple 187A; reduced stamen 2 mm long, threadlike, Yellow Green 145D, anthers reduced, pollen none.

*Phyllaries*.—In 4 leafy series, area grows to 30 mm wide and 8 mm deep, lobes lanceolate in shape, reflexed, grow to 6 mm long and 2 mm wide, Green 137A, margins strigose, tip acute, strigose on both sides.

*Receptacle*.—Grows to 10 mm wide and 10 mm deep, White NN155B.

*Bloom period*.—July through October in Canby, Oreg.

*Fragrance*.—Light.

*Lastingness*.—Each inflorescence lasts about two weeks in Canby, Oreg.

*Seeds*.—Not seen.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

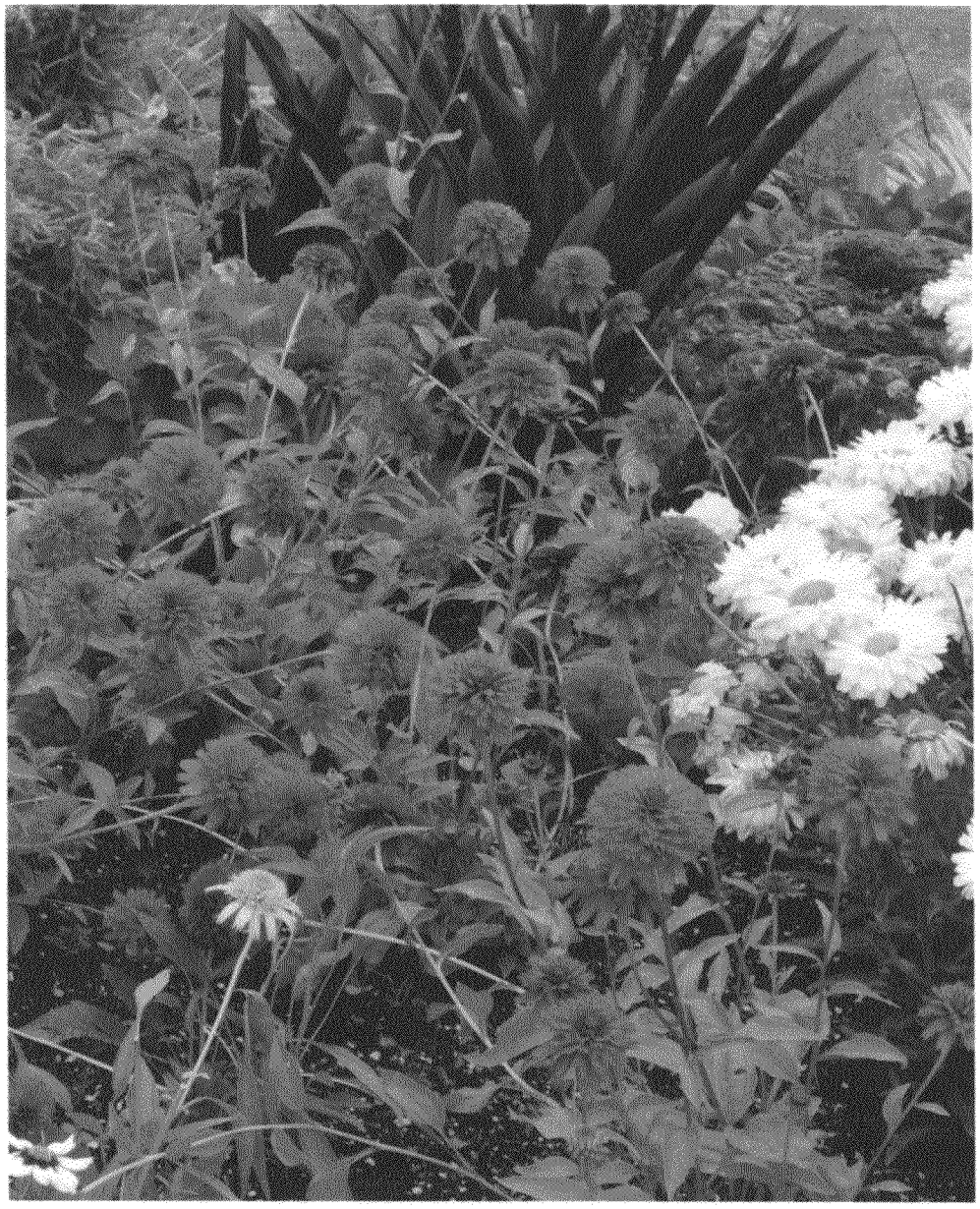

* * * * *